United States Patent
Youker et al.

(10) Patent No.: US 6,251,124 B1
(45) Date of Patent: *Jun. 26, 2001

(54) CARDIAC RHYTHM MANAGEMENT SYSTEM HAVING MULTI-CAPACITOR MODULE

(75) Inventors: Nick A. Youker, Oak Grove; Ronald L. Anderson, Lino Lakes; Sandra J. Overkamp, Moundsview, all of MN (US)

(73) Assignee: Cardiac Pacemakers, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/507,523

(22) Filed: Feb. 18, 2000

Related U.S. Application Data

(62) Division of application No. 09/073,581, filed on May 6, 1998.

(51) Int. Cl.[7] ........................................................ A61N 1/00
(52) U.S. Cl. ................................................................. 607/1
(58) Field of Search ................................... 607/1, 5, 36

(56) References Cited

U.S. PATENT DOCUMENTS

| | | | |
|---|---|---|---|
| 1,931,043 | 10/1933 | Taylor | 175/41 |
| 3,182,238 | 5/1965 | Toder et al. | 317/260 |
| 4,614,194 | 9/1986 | Jones et al. | 128/419 |
| 4,616,655 | 10/1986 | Weinberg et al. | 128/419 |
| 4,843,518 | 6/1989 | Okumura | 361/330 |
| 5,142,439 | 8/1992 | Huggett et al. | 361/321 |
| 5,195,019 | 3/1993 | Hertz | 694/328 |
| 5,367,437 | 11/1994 | Anderson | 361/807 |
| 5,428,499 | 6/1995 | Szerlip et al. | 361/328 |
| 5,493,259 | 11/1994 | Blalock et al. | 333/182 |
| 5,493,471 | 2/1996 | Walther et al. | 361/328 |

*Primary Examiner*—William E. Kamm
(74) *Attorney, Agent, or Firm*—Schwegman, Lundberg, Woessner & Kluth, P.A.

(57) ABSTRACT

A multi-capacitor module carries vertically-oriented surface mount tantalum capacitors. The module provides at least one conductor for coupling to the substrate capacitor terminals that are distal thereto. The module occupies less space, when mounted to a circuit board substrate, than individually mounting the bases of the surface mount capacitors to the substrate. This allows more efficient use of volume within an implantable cardiac rhythm management device, reducing its size, or alternatively, increasing its implanted longevity.

28 Claims, 12 Drawing Sheets

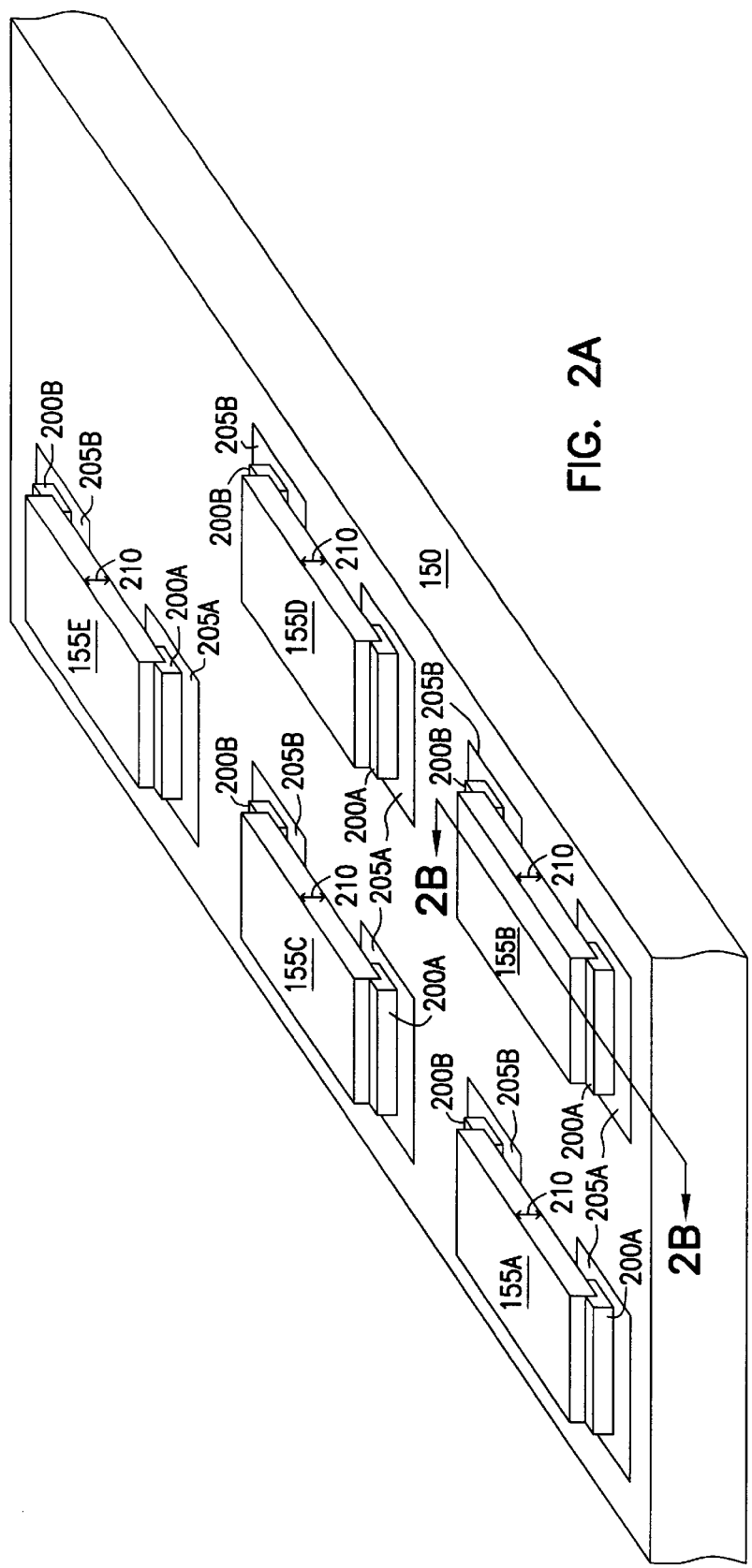

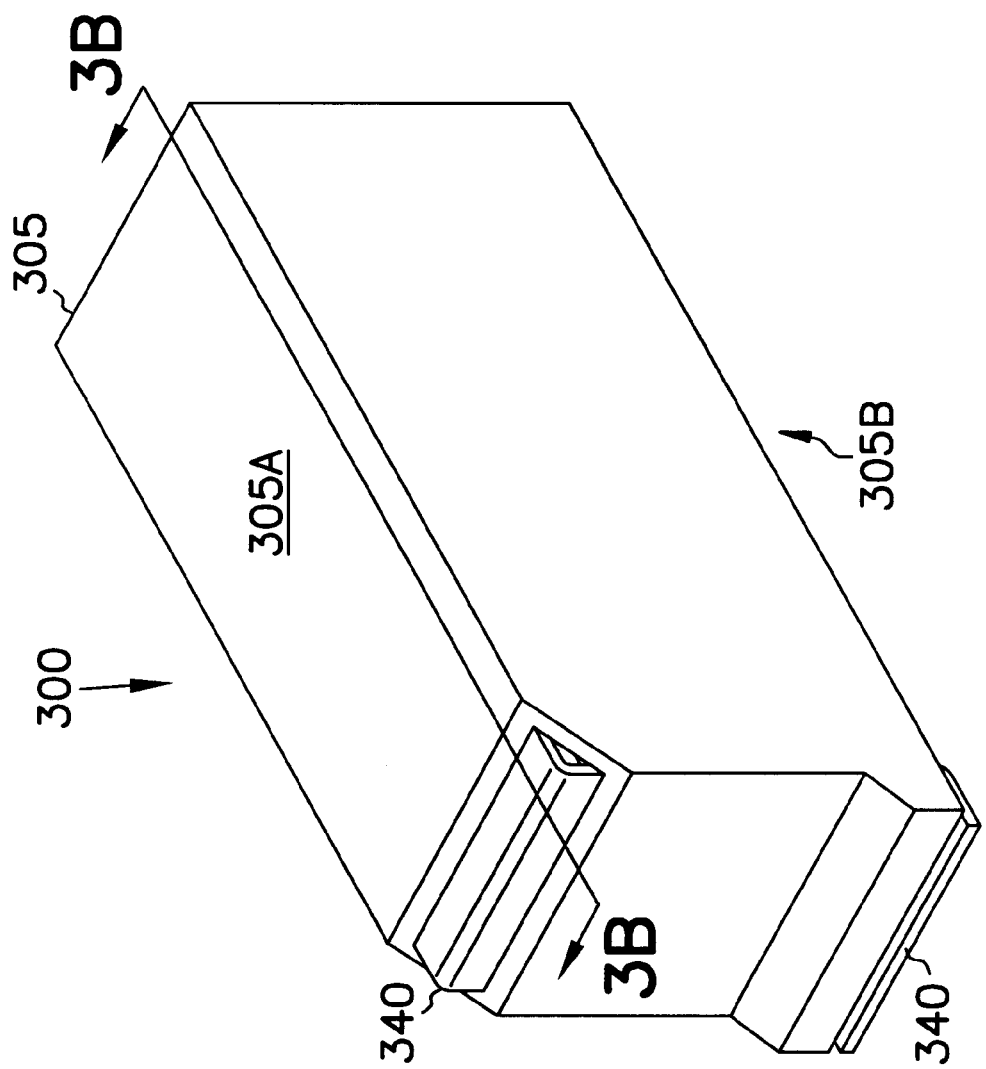

CARDIAC RHYTHM MANAGEMENT SYSTEM HAVING MULTI-CAPACITOR MODULE

This application is a division of U.S. patent application Ser. No. 09/073,581 filed May 6, 1998, (the '581 Application). The '581 Application is incorporated herein by reference.

TECHNICAL FIELD OF THE INVENTION

This invention relates generally to a multi-capacitor module and particularly, but not by way of limitation, to its use in a cardiac rhythm management system.

BACKGROUND OF THE INVENTION

Capacitors are electrical components that store electrical energy in an electromagnetic field between electrodes that are separated by a dielectric insulator. Each electrode carries a charge that is opposite in polarity to the charge on the other electrode. Capacitors find many applications in a wide variety of electric circuits. For example, implantable defibrillators and pacemakers provide cardiac rhythm management therapy to the heart in the form of low energy pacing pulses to evoke heart contractions and high energy electrical countershocks to interrupt certain arrhythmias. Such cardiac rhythm management devices include circuits that sense heart activity and control the delivery of therapy. Many of these circuits use capacitors. For example, capacitors are used to store energy for the delivery of low or high energy therapy to the heart. Capacitors are also used to in filter circuits that remove unwanted signals. In another example, capacitors are used to store energy for stabilizing power supply circuits.

One goal in designing electronic devices is to reduce the size of the electronic device, which makes the device more portable. In implantable devices, size reduction is not just important, it is critical. A smaller device is easier for the physician to implant in the patient. Moreover, by reducing the size of other components in an implantable device, a larger battery can be used, prolonging the implanted longevity of the device before a replacement device is required. Increasing the implanted longevity of such devices reduces the cost of the patient's medical treatment, which is extremely important in the present environment of rising medical costs.

Many discrete capacitors used in implantable medical devices are surface mount devices that are mounted onto multilayer hybrid substrate circuit boards. Unfortunately, such capacitors often consume a large area of the circuit board. This tends to increase the size of the implantable device, or alternatively, tends to reduce implantable longevity by reducing the battery size that can be accommodated in a particular size device. Thus, there is a critical need to more effectively use discrete capacitors in implantable medical devices and other electronic circuits.

SUMMARY OF THE INVENTION

The above-mentioned shortcomings, disadvantages and problems are addressed by the present invention, which will be understood by reading and studying the following specification and accompanying drawings that form a part thereof. The present invention provides, among other things, a multi-capacitor module. The module includes a module body having opposing top and bottom module surfaces. The module body including electrical terminals for connecting to an external circuit. The module also includes a plurality of capacitors within the module. Each capacitor is electrically coupled to terminals on the module body. Each capacitor includes a capacitor body having opposing first and second capacitor ends defining a capacitor height therebetween. The first capacitor end is adjacent to the bottom module surface. The second capacitor end is adjacent to the bottom module surface. One of the first and second capacitor ends defines a length and a width of the capacitor. The capacitor height is longer than each of the length and the width of the capacitor.

In various further embodiments, the module includes capacitors having a first and second capacitor terminals at respective first and second capacitor ends. At least one conductor is electrically coupled to at least one of the second capacitor terminals (approximately adjacent to the top module surface). The conductor extends to the bottom surface of the module. Each capacitor includes a base extending between the first and second capacitor ends. The first capacitor terminal extends partially along the base proximal to the first capacitor end. The second capacitor terminal extends partially along the base proximal to the second capacitor end.

In various further embodiments, the capacitors are tantalum capacitors (e.g., surface mount tantalum capacitors). The bottom module surface is open for accessing an interior of the module body. The terminals on the module body are located on the bottom surface of the module. In one embodiment, the present invention includes a circuit board having the above-described module mounted thereupon. In one embodiment, the circuit board comprises a hybrid circuit board substrate that includes multiple conductive and insulating layers.

Another aspect of the invention provides, among other things, a multi-capacitor module. The module includes a module body having opposing top and bottom module surfaces. Surrounding side surfaces extend between the top and bottom module surfaces. The top, bottom, and side module surfaces define an interior portion of the module therebetween. The module body includes electrical terminals for connecting to an external circuit. A plurality of tantalum capacitors are within the module. Each capacitor includes a capacitor body having opposing first and second capacitor ends defining a capacitor height therebetween. One of the first and second capacitor ends defines a length and a width of the capacitor. The capacitor height is longer than each of the length and the width of the capacitor. The capacitors are vertically disposed in a row within the module. The first capacitor ends are substantially adjacent to the bottom module surface. The second capacitor ends are substantially adjacent to the top module surface. Each capacitor includes a base extending between the first and second capacitor ends. A first capacitor terminal is located at the first capacitor end. The first capacitor terminal extends partially along the base proximal to the first capacitor end. A second capacitor terminal is located at the second capacitor end. The second capacitor terminal extends partially along the base proximal to the second capacitor end. A conductor is located substantially in the interior portion of the module. The conductor extends along the interior portion of the top module surface. The conductor is electrically coupled to each of the second capacitor terminals. The conductor also extends along the interior portion of one of the side module surfaces, and further extends to the bottom module surface. The conductor provides an electrical terminal for connecting the second capacitor terminals to an external circuit.

In various further embodiments, the present invention also includes a circuit board having the above-described module mounted-thereupon at the bottom module surface. The circuit board is electrically coupled to a portion of the conductor at the bottom module surface. The circuit board is also electrically coupled to the first capacitor terminals at the bottom module surface. In one embodiment, the circuit board comprises a hybrid circuit board substrate that includes multiple conductive and insulating layers. In a further embodiment, the conductor and the first capacitor terminals are soldered to the circuit board. In one embodiment, the module body includes a notched corner between the top module surface and one of the side module surfaces, and five capacitors are carried within the module.

Another aspect of the invention provides, among other things, a cardiac rhythm management system. The system includes a housing, a battery within the housing, and a hybrid circuit board substrate, within the housing, The substrate includes multiple conductive and insulating layers. A multi-capacitor module is mounted to the substrate. The multi-capacitor module includes a module body having opposing top and bottom module surfaces. The module body includes electrical terminals that are electrically coupled to the substrate. The bottom module surface is mounted to the substrate. A plurality of capacitors is carried within the module.

In various further embodiments, the capacitors are surface mount tantalum capacitors. Each capacitor is electrically coupled to terminals on the module body. Each capacitor includes a capacitor body having opposing first and second capacitor ends defining a capacitor height therebetween. One of the first and second capacitor ends defines a length and a width of the capacitor. The first capacitor end is approximately adjacent to the substrate. The capacitor height is longer than each of the length and the width of the capacitor. Each capacitor includes first and second capacitor terminals at the respective first and second capacitor ends. At least one conductor is electrically coupled to at least one of the second capacitor terminals. The conductor extends to the bottom surface of the module. The conductor provides one of the terminals, on the module body, that is electrically coupled to the substrate.

In various further embodiments, each capacitor includes a base extending between the first and second capacitor ends. The first capacitor terminal extends partially along the base proximal to the first capacitor end. The second capacitor terminal extends partially along the base proximal to the second capacitor end. In one embodiment, the bottom module surface advantageously occupies less mounting area on the surface of the substrate than areas of the bases summed over the plurality of the capacitors. In one embodiment, the first capacitor terminals provide terminals, on the module body, that are electrically coupled to the substrate. The bottom module surface is open for accessing an interior of the module body.

Another aspect of the invention provides, among other things, a method of forming a multi-capacitor module. A module body is formed to include opposing top and bottom module surfaces, and to include electrical terminals for connecting to an external circuit. A plurality of surface mount capacitors are disposed within the module. Each capacitor includes a capacitor body having opposing first and second capacitor ends defining a capacitor height therebetween. One of the first and second capacitor ends defining a length and a width of the capacitor. The capacitor height is longer than each of the length and the width of the capacitor.

Another aspect of the invention provides, among other things, a method of making a cardiac rhythm management system. A housing is formed. A battery is disposed within the housing. A hybrid circuit board substrate, including multiple conductive and insulating layers, is disposed within the housing. A multi-capacitor module is mounted on the substrate. The module includes a module body having opposing top and bottom module surfaces. A plurality of capacitors is disposed within the module. In a further embodiment, disposing the plurality of capacitors includes disposing a plurality of surface mount tantalum capacitors within the module.

Another aspect of the invention provides, among other things, a method of using a plurality of capacitors. Each capacitor includes opposing first and second capacitor ends defined by a capacitor length and a capacitor width. The capacitor includes a base defining a capacitor height that is longer than each of the capacitor length and width. The capacitors are inserted into a multi-capacitor module having opposing top and bottom module surfaces such that the first capacitor ends are approximately parallel and proximal to the bottom module surface. The bottom module surface is open (such as for allowing insertion of the capacitors). The bottom module surface is mounted to a hybrid circuit board substrate.

In various further embodiments, the method includes electrically coupling a terminal on each second capacitor end to the substrate, such as by contacting the terminal on at least one of the second capacitor ends using a conductor and attaching the conductor to the substrate. In one embodiment, attaching the conductor to the substrate includes soldering the conductor to the substrate. A terminal on each first capacitor end is electrically coupled to the substrate. In one embodiment, electrically coupling the terminals on each first capacitor end to the substrate includes soldering the terminals on each first capacitor end to the substrate.

Another aspect of the invention provides, among other things, a method of mounting surface mount capacitors on a circuit board. Each capacitor includes a solid rectangular shape that includes a base having electrical contacts at opposing ends of the base. A plurality of the capacitors are inserted vertically into a module having opposing top and bottom module surfaces. The module includes side module surfaces extending between the top and bottom module surfaces. The capacitors are inserted such that the base of the capacitor is parallel to one of the side module surfaces. The electrical contacts at opposing ends of the base of the capacitor are proximal to the respective top and bottom module surfaces. The electrical contacts that are proximal to the bottom module surface are electrically coupled to the board. The electrical contacts that are proximal to the top module surface are electrically coupled to the board via a conductor extending therebetween.

In summary, the present invention provides, among other things, a multi-capacitor module for carrying vertically-oriented surface mount capacitors. The module provides at least one conductor for coupling to the substrate capacitor terminals that are distal thereto. The module occupies less space, when mounted to a circuit board substrate, than individually mounting the bases of the surface mount capacitors to the substrate. This allows more efficient use of volume within an implantable cardiac rhythm management device, reducing its size, or alternatively, increasing its implanted longevity. Other advantages will become apparent upon reading the following detailed description of the invention and viewing the accompanying drawings that form a part thereof.

BRIEF DESCRIPTION OF THE DRAWINGS

In the drawings, like numerals describe substantially similar components throughout the several views. Shapes

FIG. 2A is a schematic diagram of a perspective view illustrating generally an arrangement of surface mount capacitors on a substrate.

FIG. 3A is a schematic diagram illustrating generally an exterior perspective view of a multi-capacitor module.

DETAILED DESCRIPTION OF THE INVENTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

The present invention provides, among other things, a multi-capacitor module for use in a cardiac rhythm management system or other electrical circuit. The multi-capacitor module includes surface mount capacitors that are arranged to minimize the space occupied on a hybrid circuit board. This helps reduce the volume of the implantable cardiac rhythm management system or, alternatively, increases its implanted longevity. Other advantages of the present invention will also become apparent by reading the following detailed description of the invention and viewing the accompanying drawings which form a part thereof.

Figure 1:
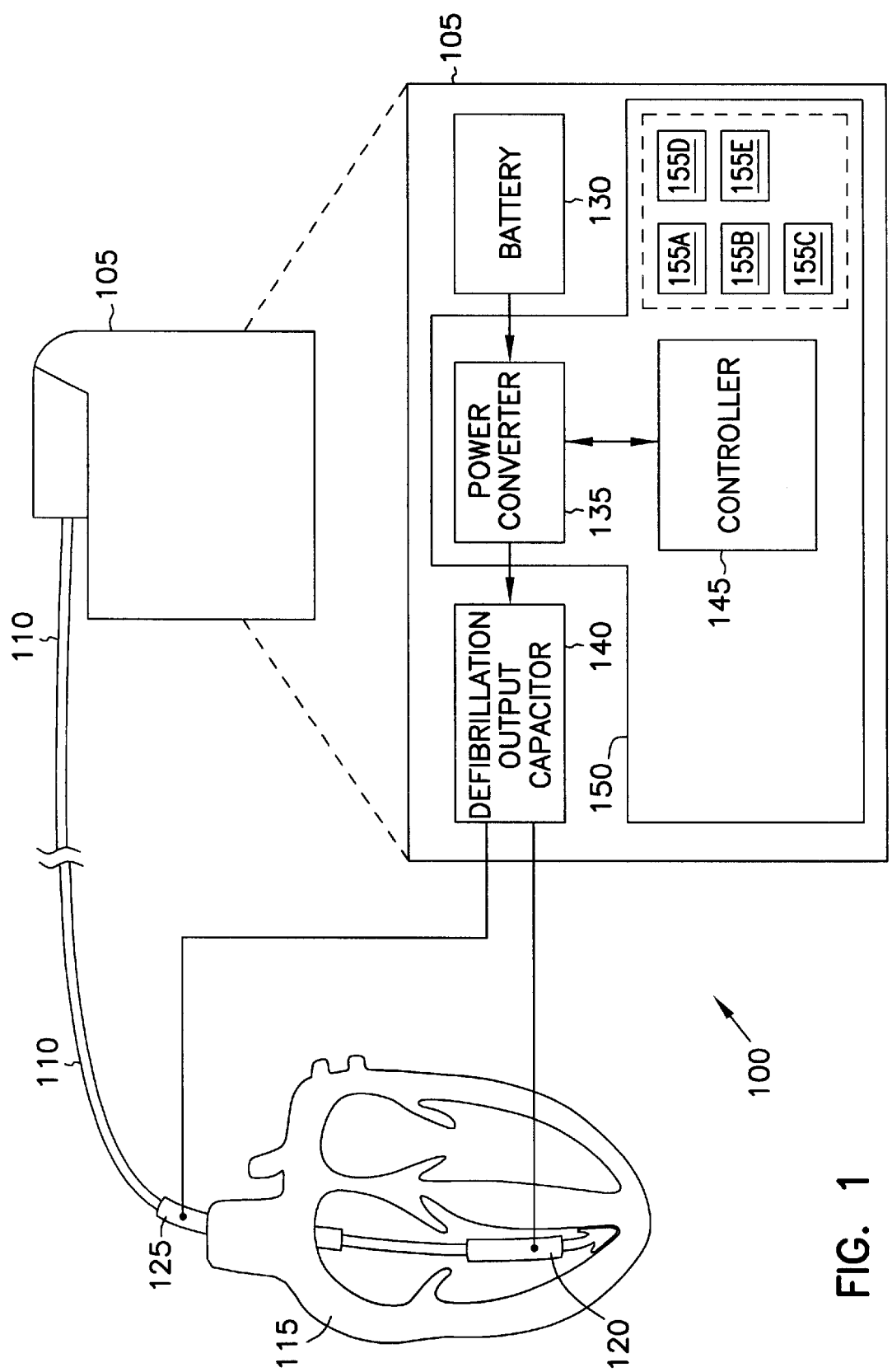
FIG. 1 is a schematic/block diagram illustrating generally one embodiment of a cardiac rhythm management system.

FIG. 1 is a schematic/block diagram illustrating generally, by way of example, but not by way of limitation, one embodiment of a cardiac rhythm management system 100 according to one aspect of the present invention. System 100 includes, among other things, cardiac rhythm management device 105 and leadwire ("lead") 110 for communicating signals between device 105 and a portion of a living organism, such as a heart 115. In the illustrated example, device 105 includes an automatic implantable cardioverter/defibrillator (AICD), but any other apparatus for cardiac rhythm management is also included within the present invention.

In the illustrated embodiment, portions of system 100 is implantable in the living organism, such as in a pectoral or abdominal region of a human patient, or elsewhere. In another embodiment, portions of system 100 (e.g., device 105) are alternatively disposed externally to the human patient. In the illustrated embodiment, portions of lead 110 are disposed in the right ventricle, however, any other positioning of lead 110 is included within the present invention. In one embodiment, lead 110 is a commercially available endocardial defibrillation lead. System 100 can also include other leads in addition to lead 110, appropriately disposed, such as in or around heart 115, or elsewhere.

In one example, a first conductor of multiconductor lead 110 electrically couples a first electrode 120 to device 105. A second conductor of multiconductor lead 110 independently electrically couples a second electrode 125 to device 105. Device 105 includes an energy source, such as battery 130, a power converter 135, such as a flyback converter, at least one defibrillation output capacitor 140, and a controller 145 for controlling the operation of device 105. In one embodiment, power converter 135 transforms the terminal voltage of battery 130, which is approximately between 2 Volts and 3.25 Volts, into a 750 Volt defibrillation output energy pulse stored on the defibrillation output capacitor 140. In another embodiment, power converter 135 transforms the terminal voltage of two series-coupled batteries, which is approximately between 4 Volts and 6.25 Volts, into the 750 Volt defibrillation output energy pulse stored on the defibrillation output capacitor 140.

In the illustrated embodiment, various electrical components, including both discrete components and monolithic integrated circuits (e.g., portions of power converter 135 and controller 145), within device 105 are located on at least one multilayer hybrid substrate circuit board 150 (also referred to as a "circuit board," "board," "hybrid," or "substrate.") In one embodiment, discrete surface mount tantalum capacitors 155A–E are mounted to substrate 150, as discussed below. In one example, tantalum capacitors 155A–E are power supply stabilization capacitors that interface with regulated power supply circuits in controller 145. However, the present invention also includes any other circuits using discrete capacitors mounted on substrate 150.

FIG. 2A is a schematic diagram of a perspective view illustrating generally one embodiment of a conventional arrangement of surface mount capacitors 155A–E on substrate 150. The surface mount capacitors 155 each have a solid rectangular shape, as illustrated in FIG. 2A. In one embodiment, by way of example, but not by way of limitation, capacitors 155 include a plurality (e.g., five) tantalum capacitors. A base of each capacitor 155 is mounted to substrate 150 such that conductive electrical contacts 200A–B, at opposing ends of the bases and extending partially along the corresponding sides, make physical and electrical contact with corresponding conductive electrical contact landing pads 205A–B on the surface of substrate 150. In one embodiment, mounting capacitors 155 to substrate 150 includes soldering electrical contacts 200A–B on the capacitors to corresponding pads 205A–B on substrate 205.

As seen in FIG. 2A, the typical low-profile (i.e., having a small vertical dimension 210), oblong solid rectangular shape of surface mount tantalum capacitors 155 results in capacitors 155 occupying considerable area on the surface of substrate 150. Pads 205 require the use of even more space on substrate 105. Moreover, pad-to-pad spacing requirements are imposed in order to ensure electrical isolation between pads 205 after capacitors 155 are soldered or otherwise mounted to substrate 150. This further increases the space occupied by the capacitors 155 on substrate 150. The small vertical dimension 210 results in wasted space within device 150 when other higher-profile components (e.g., a toroidal coil, having a larger vertical dimension, used in power converter 135) are also mounted on substrate 150.

Figure 2B:
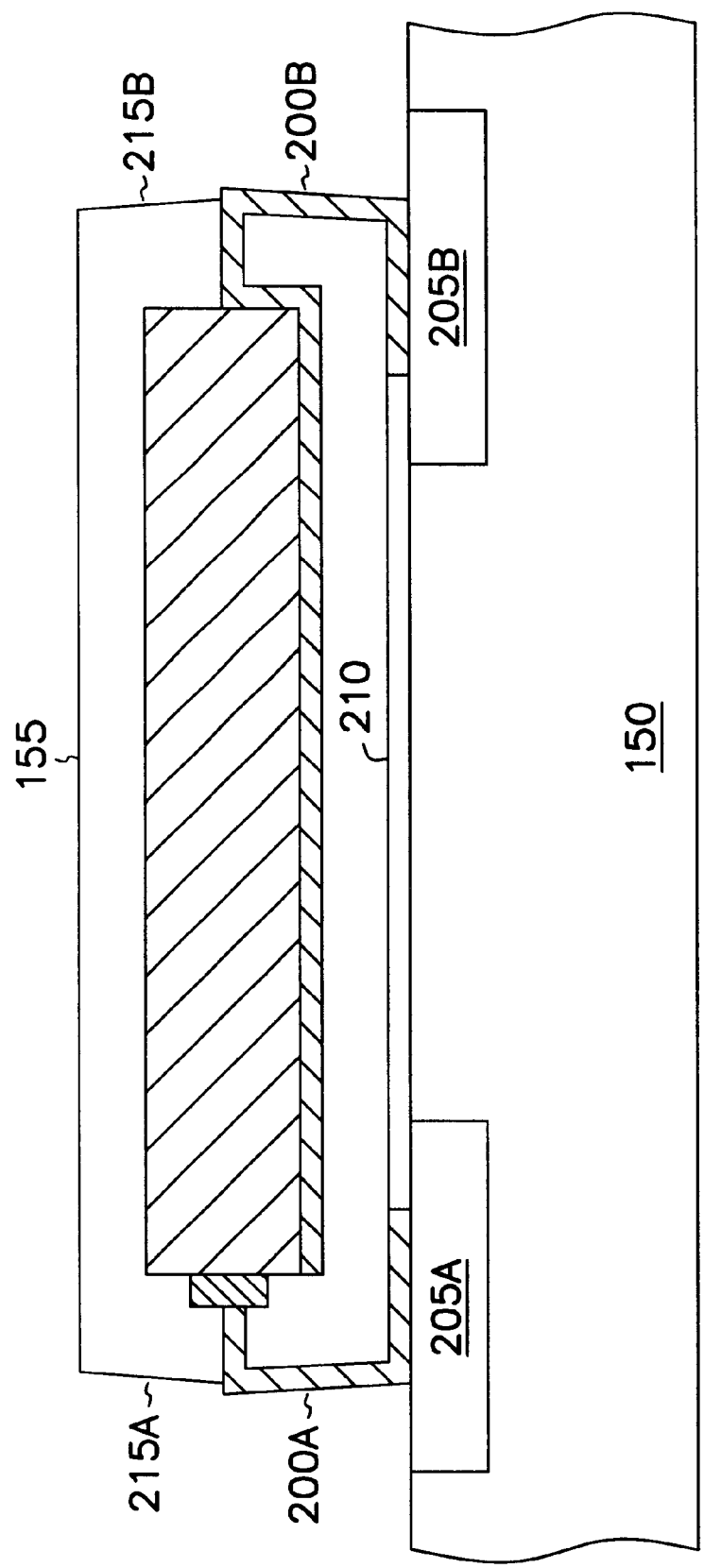
FIG. 2B is a schematic diagram, taken along the cutline 2B—2B of FIG. 2A, illustrating generally a cross-sectional view of one embodiment of a capacitor.

FIG. 2B is a schematic diagram, taken along the cutline 2B—2B of FIG. 2A, that illustrates generally a cross-sectional view of one embodiment of a capacitor 155. In FIG. 2B, contacts 200A–B extend along the base 210 of capacitor 155, and also partially along the corresponding first end 215A and second end 215B of the capacitor 155 before entering the interior of capacitor 155 for making contact to its anode and cathode regions.

One aspect of the present invention provides more efficient utilization of the surface area of substrate 150 than is shown in FIGS. 2A and 2B. This is accomplished by disposing capacitors 155 vertically on substrate 150, in spite of the fact that typical surface mount capacitors 155 have electrical contacts 200 only on opposing ends of their bases 210 (i.e., near first end 215A and second end 215B). The present invention includes, among other things, rotating the capacitors 155 to extend longitudinally outward from substrate 150. This decreases the surface area on substrate 150 that is occupied by the capacitors 155, as discussed below.

Figure 3B:
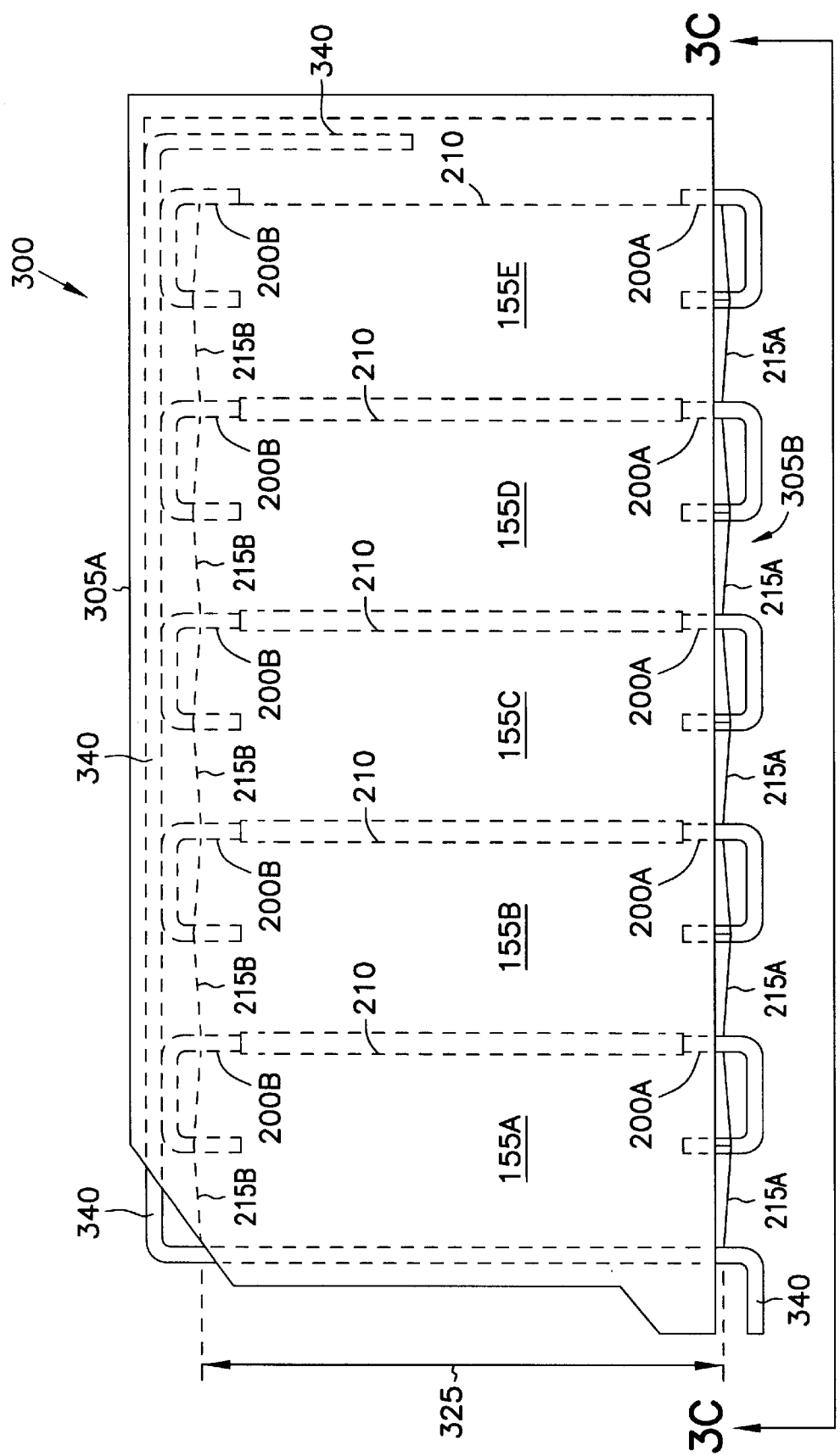
FIG. 3B is a schematic diagram illustrating generally a cross-sectional side view of the multi-capacitor module taken along the cutline 3B—3B in FIG. 3A.
Figure 3C:
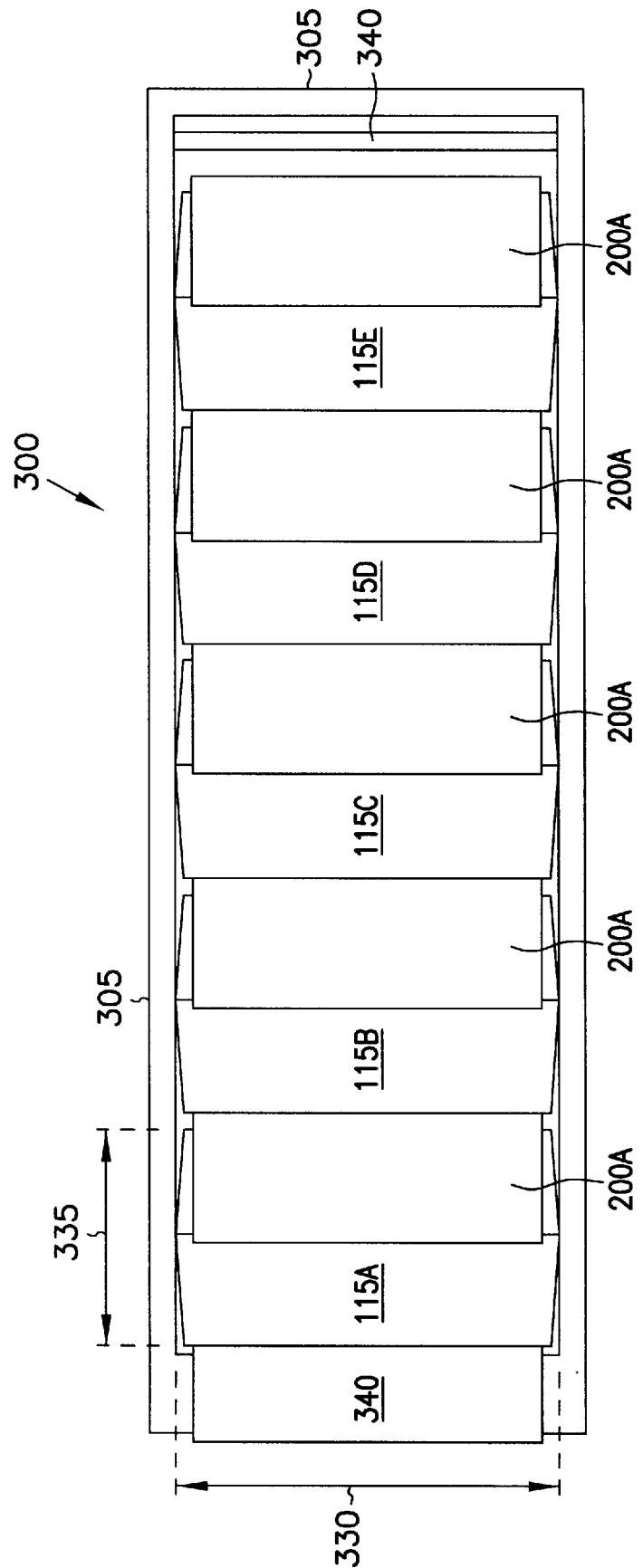
FIG. 3C is a schematic diagram illustrating generally a bottom view of the multi-capacitor module taken along the cutline 3C—3C in FIG. 3B.

FIGS. 3A, 3B, and 3C are schematic diagrams illustrating generally a multi-capacitor module 300, illustrated in an exterior perspective view (FIG. 3A), a cross-sectional side view (FIG. 3B), taken along the cutline 3B—3B in FIG. 3A, and a bottom view (FIG. 3C), taken along the cutline 3C—3C in FIG. 3B. The dimensions illustrated are by way of example only, and not by way of limitation.

In FIG. 3A, a module body 305 forms an approximately solid rectangular shape, and includes a top surface 305A, an open bottom surface 305B, and four side surfaces extending between top surface 305A and bottom surface 305B, thereby defining an open interior portion of module body 305 into which capacitors 155 are inserted. According to one aspect of the invention, bottom surface 305B is mounted to a circuit board such as hybrid substrate 150.

FIG. 3B illustrates a cross-sectional view of multi-capacitor module 300 taken along the cutline 3B—3B of FIG. 3A. In FIG. 3B, capacitors 155A–E have been inserted into module body 305 through its open bottom surface 305B. In the vertical orientation of FIG. 3B, each capacitor 155 includes its first end 215A being approximately parallel and proximal to bottom surface 305B of module 300, and its second end 215B being approximately parallel and proximal to top surface 305A of module 300. First end 215A and second end 215B are oriented as respective bottom and top capacitor surfaces in FIG. 3B, and are oriented as side surfaces in the conventional orientation of FIG. 2B. In FIG. 3B, base 210 is vertically oriented outward from substrate 150. By contrast, in the conventional orientation of the surface mount capacitor 155 illustrated in FIG. 2B, base 210 of capacitor 155 is horizontally-oriented to be approximately parallel to substrate 150 for conventional mounting thereto. Each contact 200B is located substantially adjacent to the top surface 305A of the interior portion of module body 305. Each contact 200A is located substantially adjacent to the open bottom surface 305B.

First and second ends 215A–B of the capacitors 155 define a height 325 therebetween. Each of first and second ends 215A–B are approximately rectangular, and define a length 330 and width 335, as illustrated in FIG. 3C. According to one aspect of the invention, capacitor height 325 is longer than each of the length 330 and width 335 of the capacitor 155. As a result, the plurality of capacitors 155A–E occupies less surface area of substrate 150 when the bottom surface 305 of module 300 is mounted to substrate 150 than when the bases 210 are mounted directly to substrate 150 as illustrated in FIGS. 2A and 2B.

FIGS. 3A, 3B, and 3C include at least one conductor 340 for coupling contacts 200B on the second ends 215B of the capacitors 155A–E to at least one landing pad on substrate 150. Contacts 200A of capacitors 155A–E are directly coupled (e.g., solder-mounted) to separate or common landing pads on substrate 150. FIG. 3B illustrates one embodiment, by way of example, but not by way of limitation, in which the contacts 200B on each capacitor 155A–E are commonly electrically coupled to substrate 150 by a single conductor 340. Conductor 340 extends along the interior of top surface 305A of module 300, and along a side of module 300 to the bottom surface 305B of module 300 where it is solder-mounted or otherwise coupled to a corresponding landing pad on substrate 150. While those portions of contacts 200B extending along the respective bases 210 of the capacitors 155 are ordinarily used for electrically coupling to the capacitor 155, one embodiment of the present invention advantageously allows those portions of contacts 200B extending along the respective second ends 215B for electrically coupling external circuits to the capacitors 155 via conductor 340.

In one embodiment, a portion of conductor 340 extends along the interior portion of the top surface 305A of module 300, and along a side of module 300 to the bottom surface 305B of module 300, and optionally extends at least partially along an opposing side of module 300, as illustrated in FIG. 3B. In another embodiment, a corner of the top surface 305A is optionally notched, thereby exposing a portion of conductor 340, as illustrated in FIG. 3A.

Figure 3D:
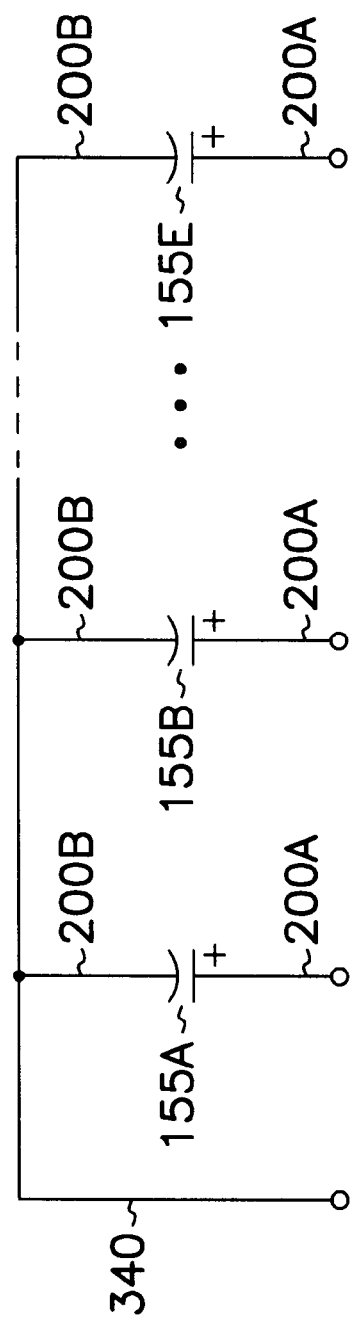
FIGS. 3D, and 3E are schematic diagrams illustrating generally particular configurations of interconnecting the capacitors.
Figure 3E:
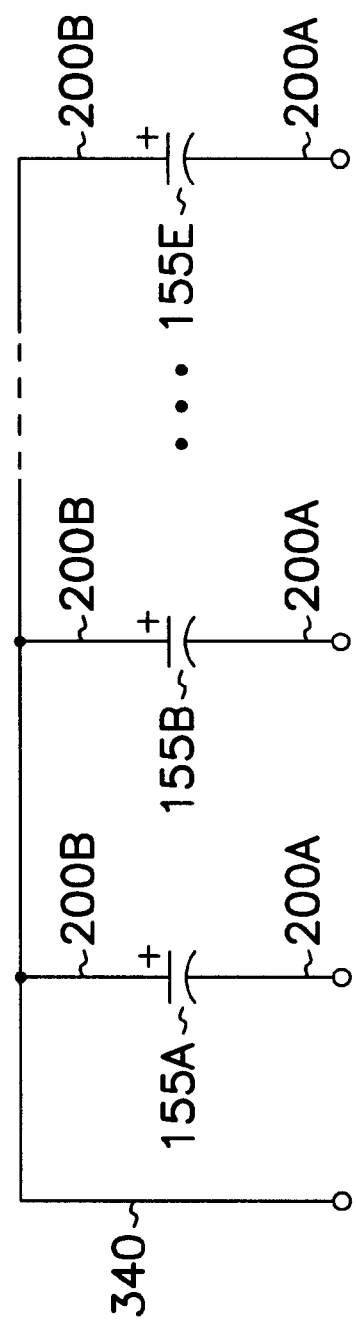

FIGS. 3D and 3E are schematic diagrams illustrating generally, by way of example, but not by way of limitation, particular configurations of interconnecting the capacitors 155. In FIGS. 3D and 3E, capacitors 155 are polar; the polarity of capacitors 155 can be interchanged either as shown, or in any other suitable arrangement to meet circuit design requirements.

Figure 4A:
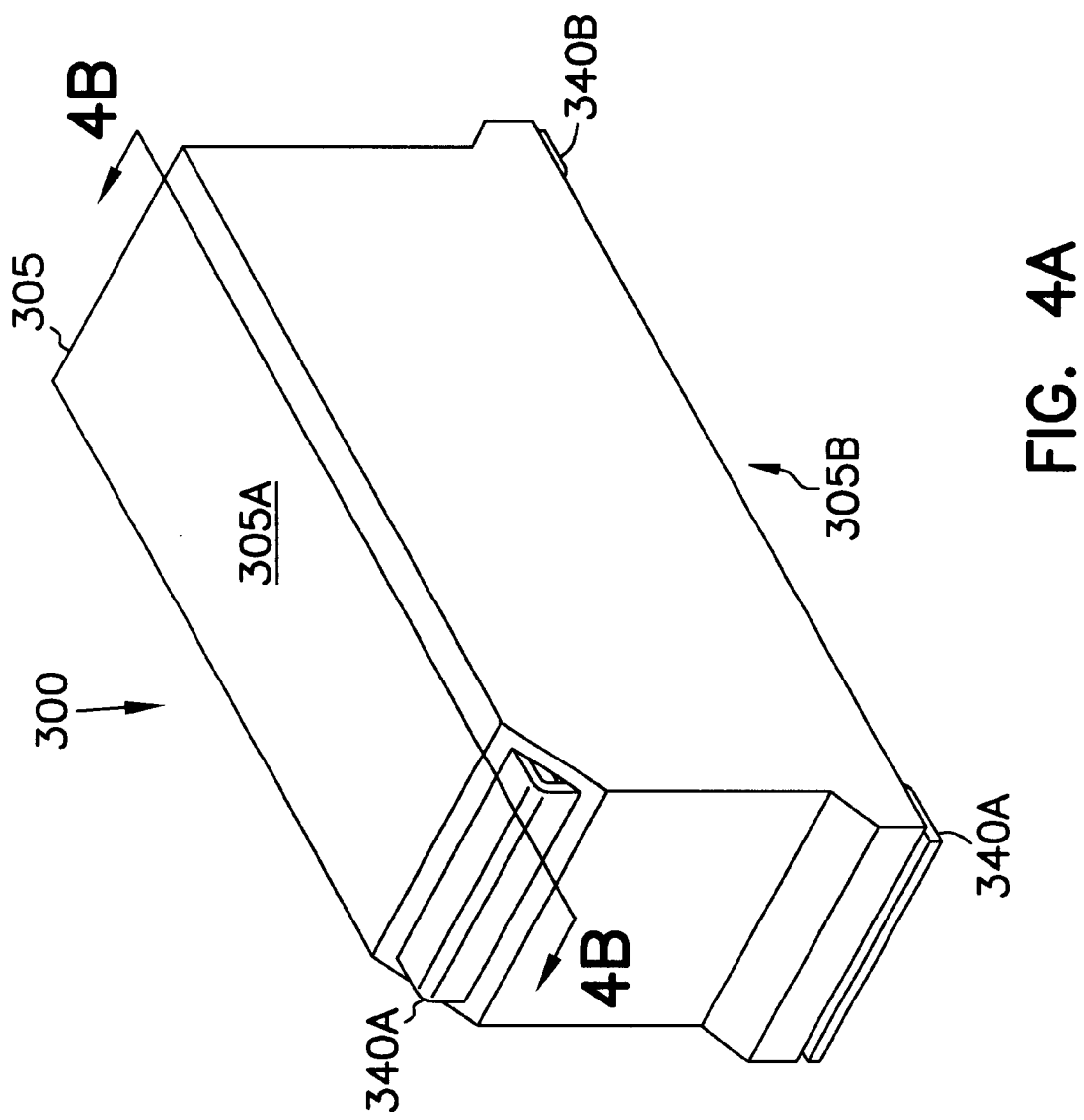
FIG. 4A is a schematic diagram illustrating generally an exterior perspective view of another embodiment of a multi-capacitor module.
Figure 4B:
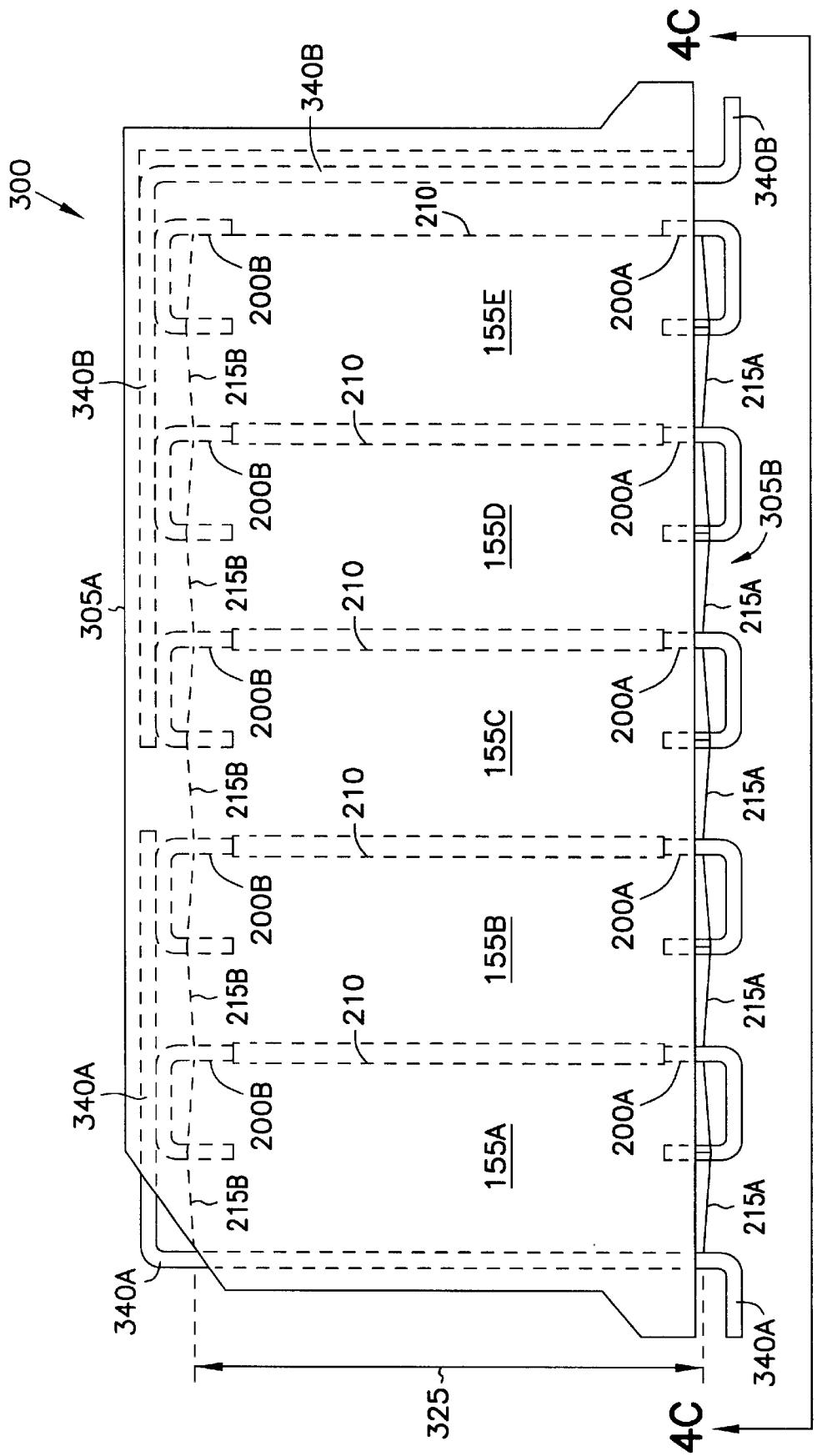
FIG. 4B is a schematic diagram illustrating generally a cross-sectional side view of the multi-capacitor module taken along the cutline 4B—4B in FIG. 4A.
Figure 4C:
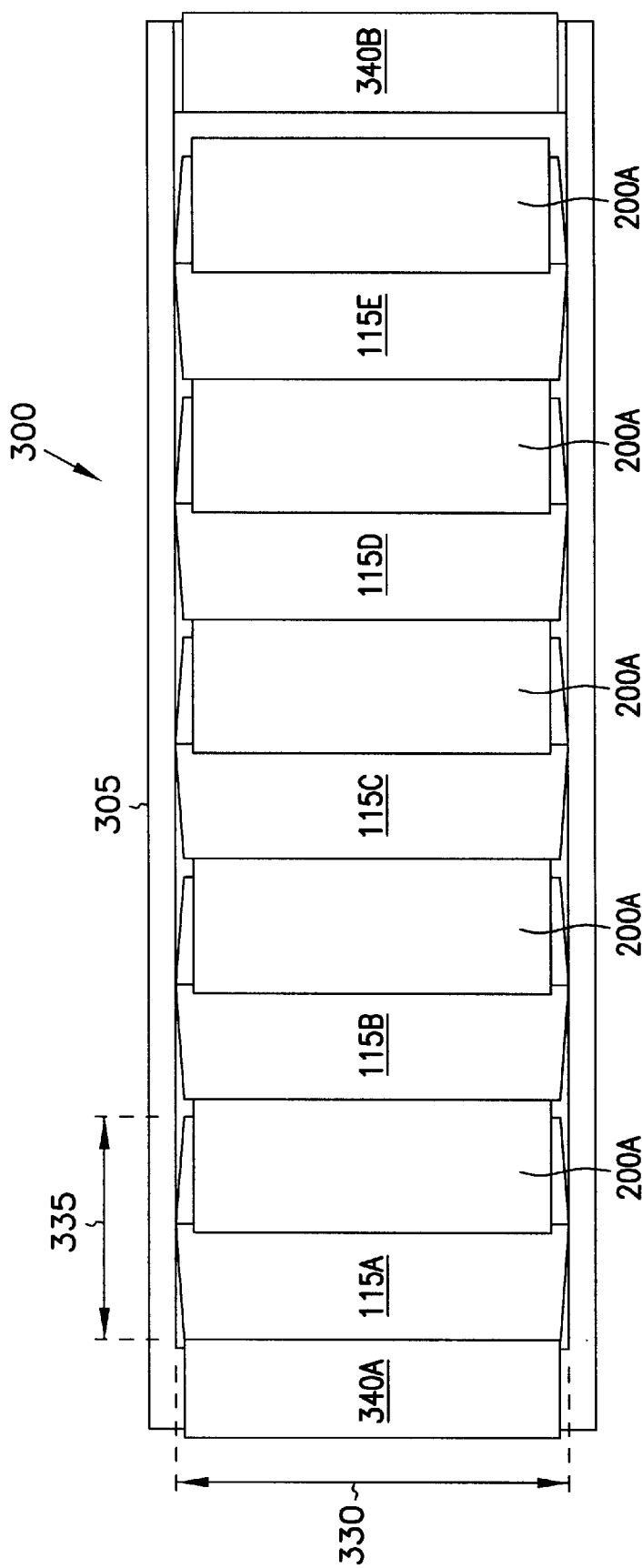
FIG. 4C is a schematic diagram illustrating generally a bottom view of the multi-capacitor module taken along the cutline 4C—4C in FIG. 4B.

FIGS. 4A, 4B, and 4C are schematic diagrams, corresponding generally to the views illustrated respective FIGS. 3A, 3B, and 3C, of another embodiment of the present invention. FIGS. 4A, 4B, and 4C illustrate the use of multiple conductors 340A and 340B. In this embodiment, by way of example, but not by way of limitation, contacts 200B of capacitors 155A–B are coupled to a the substrate via conductor 340A. Contacts 200B of capacitors 155C–E are coupled to the substrate via conductor 340B. Contacts 200A of capacitors 155A–E are directly coupled (e.g., solder-mounted) to separate or common landing pads on substrate 150. Additional conductors 340 for individually coupling contacts 200B to substrate 150 can also be included (e.g., extending down the same or different sides of module body 305).

Figure 4D:
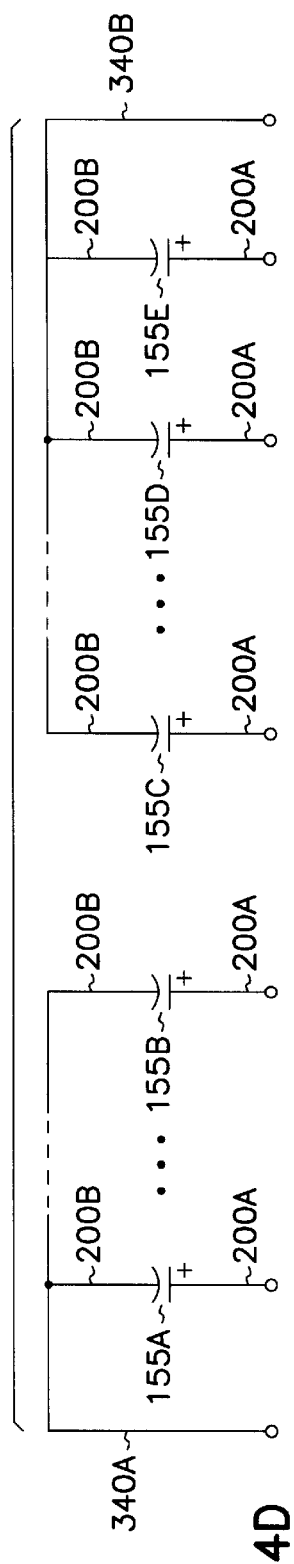
FIGS. 4D, 4E, and 4F are schematic diagrams illustrating generally particular configurations of interconnecting the capacitors.
Figure 4E:
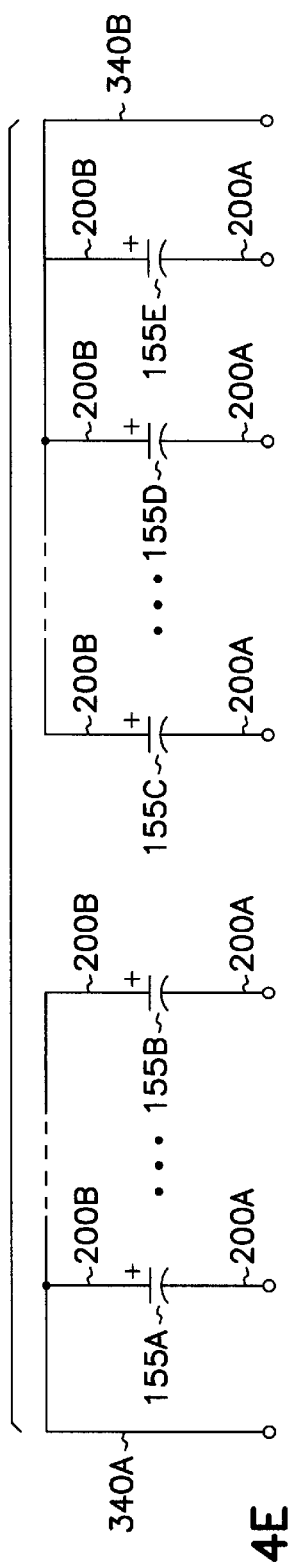
Figure 4F:
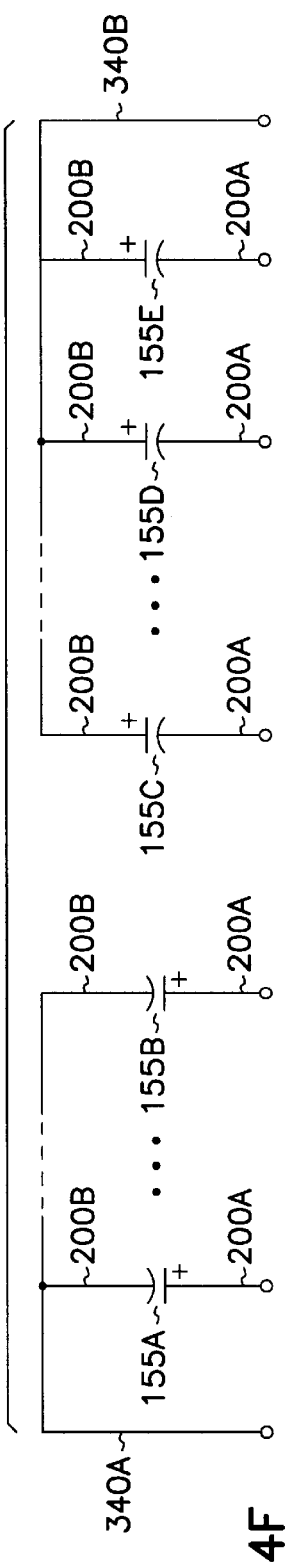

FIGS. 4D, 4E, and 4F are schematic diagrams illustrating generally, by way of example, but not by way of limitation, particular configurations of interconnecting the capacitors 155. In FIGS. 4D–4F, capacitors 155 are polar; the polarity of capacitors 155 can be interchanged either as shown, or in any other suitable arrangement to meet circuit design requirements.

Figure 5B:
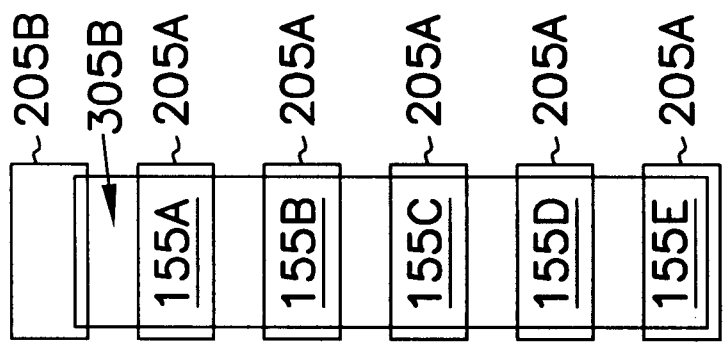
FIG. 5B is a schematic diagram of a plan view of surface mount capacitors that are vertically disposed in a module mounted to the substrate.
Figure 5A:
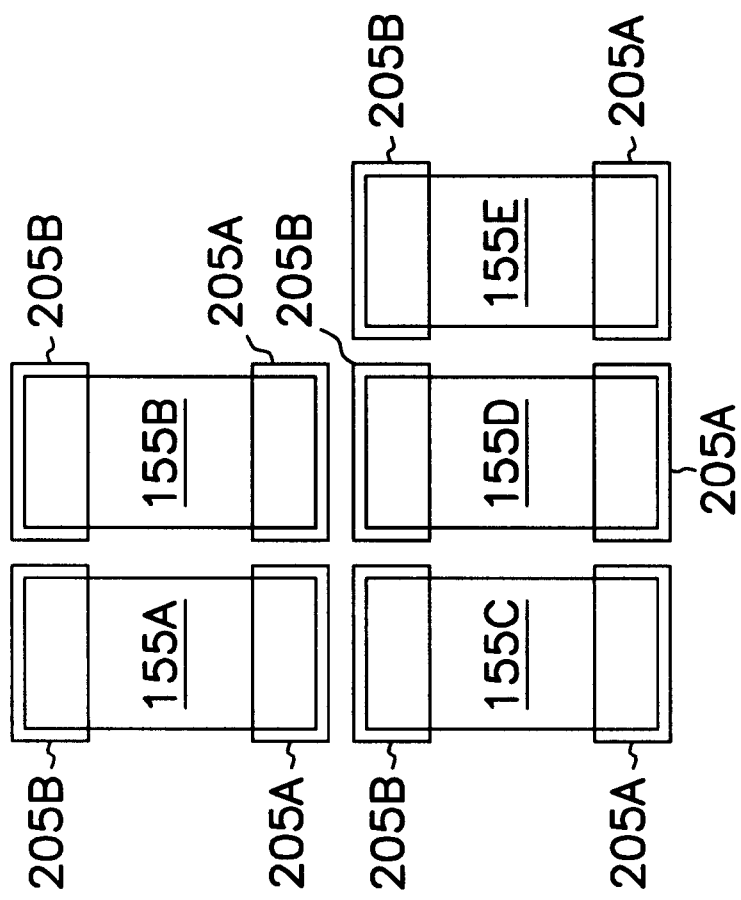
FIG. 5A is a schematic diagram of a plan view of surface mount capacitors having bases mounted directly to a substrate.

FIGS. 5A and 5B are schematic diagrams illustrating generally respective plan views, looking down toward the surface of substrate 150, of one arrangement of conventionally mounted surface mount capacitors 155A–E, having the "footprint" illustrated by FIG. 5A, and another arrangement of the same capacitors 155A–E vertically disposed in module 300, according to the present invention, having the footprint illustrated by FIG. 5B. A comparison of FIGS. 5A and 5B illustrates the dramatic reduction (by a factor of approximately $\frac{2}{3}$) in surface area of substrate 150 occupied by the capacitors 155A–E in the arrangement of FIG. 5B as compared to the conventional arrangement illustrated in FIG. 5A.

Reducing the amount of surface area required for mounting capacitors 155 to substrate 150 is particularly advantageous when enough space exists in a vertical dimension (outward from the surface of substrate 150) to accommodate the taller vertically-oriented surface mount capacitors 155 carried in multi-capacitor module 300. For example, as discussed above, when substrate 150 is already populated with higher-profile discrete components (e.g., a toroidal coil), such space is available in a direction outward from the surface of substrate 150. Other design choices may also result in space being available in a direction outward from the surface of substrate 150. The present invention allows such space to be utilized by capacitors 155 rather than remaining empty. This provides more efficient use of the volume within an implantable device 105, reducing its size, or alternatively, increasing its implanted longevity by accommodating a larger battery 130.

CONCLUSION

Thus, the present invention provides, among other things, a multi-capacitor module for carrying vertically-oriented surface mount capacitors. The module provides at least one conductor for coupling to the substrate capacitor terminals that are distal thereto. The module occupies less space, when mounted to a circuit board substrate, than individually mounting the bases of the surface mount capacitors to the substrate. This allows more efficient use of volume within an implantable cardiac rhythm management device, reducing its size, or alternatively, increasing its implanted longevity.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method of forming a multi-capacitor module, the method comprising:

forming a module body including opposing top and bottom module surfaces and including electrical terminals for connecting to an external circuit; and disposing a plurality of surface mount capacitors within the module, in which each capacitor includes a capacitor body having opposing first and second capacitor ends defining a capacitor height therebetween, one of the first and second capacitor ends defining a length and a width of the capacitor, wherein the capacitor height is longer than each of the length and the width of the capacitor.

2. The method of claim 1, further comprising forming a notch in at least one corner of the top module surfaces of the multi-capacitor module body.

3. The method of claim 2, wherein the corner of the top module surface is notched such that a portion of the conductor is exposed.

4. The method of claim 1 further comprising disposing a plurality of tantalum capacitors within the module.

5. The method of claim 4, wherein the tantalum capacitors are polar and their arrangement is interchangeable.

6. The method of claim 1, wherein disposing a plurality of capacitors includes vertically disposing the capacitors in a row within the module, the second capacitor ends being substantially adjacent to the top module surface, the first capacitor ends being substantially adjacent to the bottom module surface.

7. The method of claim 1, wherein disposing a plurality of capacitors includes disposing capacitors in which each capacitor including a base extending between the first and second capacitor ends, a first capacitor terminal at the first capacitor end and extending partially along the base proximal to the first capacitor end, and a second capacitor terminal at the second capacitor end and extending partially along the base proximal to the second capacitor end.

8. The method of claim 1, forming a module body includes providing an opening for accessing an interior of the module body.

9. The method of claim 1, forming a module body includes forming the bottom module surface such that it occupies less mounting area on a surface of the substrate than areas of the bases summed over the plurality of the capacitors.

10. The method of claim 1, further comprising disposing a plurality of surface mount capacitors, in which each capacitor includes a base extending between the first and second capacitor ends, the first terminal extends partially along the base proximal to the first capacitor end, the second capacitor terminal extends partially along the base proximal to the second capacitor end.

11. The method of claim 10, electrical coupling to a substrate is provided by the first capacitor terminal.

12. The method of claim 1, wherein a plurality of conductors are included to individually and electronically couple the second capacitor terminal at the second capacitor end to the circuit board.

13. The method of claim 1, further forming a conductor located substantially in the interior portion of the module, the conductor extending along the interior portion of the top module surface and being electrically coupled to each of the second capacitor terminals, the conductor also extending along the interior portion of one of the side module surfaces and extending to the bottom module surface and providing an electrical terminal for connecting the second capacitor terminals to an external circuit.

14. The method of claim further forming a notch in top corner of the module body so as to expose a portion of the conductor.

15. The method claim 1, further forming a plurality of conductors located substantially in the interior portion of the module, wherein a first conductor extends along the first portion of the interior portion of the top module surface and being electrically coupled to a first plurality of the second capacitor terminals, the first conductor also extends along the interior portion of a first side module surface and extends to a first portion of the bottom module surface and provides an electrical terminal for connecting the second capacitor terminals to an external circuit;

wherein further a second conductor extends along a second portion of the interior portion of the top module surface and being coupled to a second plurality of the second capacitor terminals, the second conductor also extends along the interior portion of a second side module surface and extends to a second portion of the bottom module surface and provides an electrical terminal for connecting the second capacitor terminals to an external circuit.

16. A method of using a plurality of capacitors, each capacitor having opposing first and second capacitor ends defined by a capacitor length and a capacitor width, and having a base defining a capacitor height that is longer than each of the capacitor length and width, the method comprising:

inserting the capacitors into a multi-capacitor module having opposing top and bottom module surfaces such that the first capacitor ends are approximately parallel and proximal to the bottom module surface, wherein the bottom module surface is open; and mounting the bottom module surface to a hybrid circuit board substrate.

17. The method of claim 16, further comprising electrically coupling a terminal on each second capacitor end to the substrate.

18. The method of claim 17, in which electrically coupling the terminal on each second capacitor end to the substrate includes:

contacting the terminal on at least one of the second capacitor ends using a conductor; and attaching the conductor to the substrate.

19. The method of claim 18, in which attaching the conductor to the substrate includes soldering the conductor to the substrate.

20. The method of claim 1, further comprising electrically coupling a terminal on each first capacitor end to the substrate.

21. The method of claim 20, in which electrically coupling the terminals on each first capacitor end to the substrate includes soldering the terminals on each first capacitor end to the substrate.

22. The method of claim 16, further comprising vertically disposing the capacitor in a row within the module surface.

23. The method of claim 16, further disposing a plurality of tantalum capacitors within the module.

24. A method of mounting surface mount capacitors on a circuit board, each capacitor having a solid rectangular shape that includes a base having electrical contacts at opposing ends of the base, the method comprising:

inserting a plurality of the capacitors vertically into a module having opposing top and bottom module surfaces, and having side module surfaces extending between the top and bottom module surfaces, such that the base of the capacitor is parallel to one of the side module surfaces, and the electrical contacts at opposing ends of the base of the capacitor are proximal to the respective top and bottom module surfaces;

electrically coupling the electrical contacts that are proximal to the bottom module surface to the board; and electrically coupling the electrical contacts that are proximal to the top module surface to the board via a conductor extending therebetween.

25. The method of claim 24, wherein each surface mount capacitor includes a capacitor body having opposing first and second capacitor ends defining a capacitor height therebetween, one of the first and second capacitor ends defining a length and a width of the capacitor, wherein the capacitor height is longer than each of the length and the width of the capacitor, the capacitors being vertically disposed in a row within the module, the second capacitor ends being substantially adjacent to the top module surface, each capacitor including a base extending between the first and second capacitor ends, a first capacitor terminal at the first capacitor end and extending partially along the base proximal to the first capacitor end, and a second capacitor terminal at the second capacitor end and extending partially along the base proximal to the second capacitor end.

26. The method of claim 25, further includes extending the conductor along an interior portion of one of a plurality of side module surfaces and extending to the bottom module surface and providing an electrical terminal for connecting the second capacitor terminals to an external circuit.

27. The method of claim 24, further soldering the electrical contacts that are proximal to the bottom module surface to the board.

28. The method of claim 24, wherein inserting a plurality of the capacitors vertically includes disposing the capacitors in a row within the module, a first capacitor end being substantially adjacent to the bottom module surface, the second capacitor end being substantially adjacent to the top module surface.

* * * * *

UNITED STATES PATENT AND TRADEMARK OFFICE
CERTIFICATE OF CORRECTION

PATENT NO.   : 6,251,124 B1
DATED        : June 26, 2001
INVENTOR(S)  : Youker et al.

It is certified that error appears in the above-identified patent and that said Letters Patent is hereby corrected as shown below:

Column 10, claim 14,
Line 65, delete "claim further" and insert -- claim 13, further --, Column 11, claim 20,
Line 46, delete "claim 1" and insert -- claim 16 --, therefor.

Signed and Sealed this

Ninth Day of April, 2002

Attest:

Attesting Officer

JAMES E. ROGAN
Director of the United States Patent and Trademark Office